United States Patent [19]

DiMaio et al.

[11] Patent Number: 5,255,303
[45] Date of Patent: Oct. 19, 1993

[54] MULTI-PURPOSE EMERGENCY ROOM TRAUMA BOARD

[75] Inventors: J. Michael DiMaio; James D. Dalton, Jr., both of Durham, N.C.

[73] Assignee: Duke University, Durham, N.C.

[21] Appl. No.: 977,804

[22] Filed: Nov. 17, 1992

[51] Int. Cl.⁵ .................................................. H05G 1/02
[52] U.S. Cl. ..................................... 378/177; 378/208; 5/601; 5/625
[58] Field of Search ............... 378/208, 209, 177; 5/601, 82 R, 89.1, 625

[56] References Cited

U.S. PATENT DOCUMENTS

| | | | |
|---|---|---|---|
| 2,926,054 | 2/1960 | Rodin | 311/5 |
| 3,358,141 | 4/1965 | Hoffmann et al. | 250/50 |
| 3,648,305 | 3/1972 | Ersek | 5/82 |
| 3,655,178 | 4/1972 | Vezina | 269/323 |
| 3,947,686 | 3/1976 | Cooper et al. | 250/439 |
| 4,067,565 | 1/1978 | Daniels | 269/328 |
| 4,193,148 | 3/1980 | Rush | 5/86 |
| 4,635,914 | 1/1987 | Kabanek | 269/328 |
| 4,653,482 | 3/1987 | Kurland | 128/71 |
| 4,779,858 | 10/1988 | Saussereau | 269/328 |
| 4,947,418 | 8/1990 | Barr et al. | 378/177 |
| 4,995,067 | 2/1991 | Royster et al. | 378/177 |
| 5,016,268 | 5/1991 | Lotman | 378/209 |

Primary Examiner—David P. Porta
Assistant Examiner—Don Wong
Attorney, Agent, or Firm—Richard E. Jenkins

[57] ABSTRACT

A multi-purpose emergency room trauma board having a rigid plastic backboard which is removably mounted in parallel and spaced-apart fashion on a rigid base. The rigid base includes an elevated lip around the perimeter thereof to define a drip pan on the top surface thereof and support means mounted thereon to removably support the backboard in spaced-apart relationship to the base at a sufficient height to allow slidable positioning of an X-ray cassette therebetween.

14 Claims, 6 Drawing Sheets

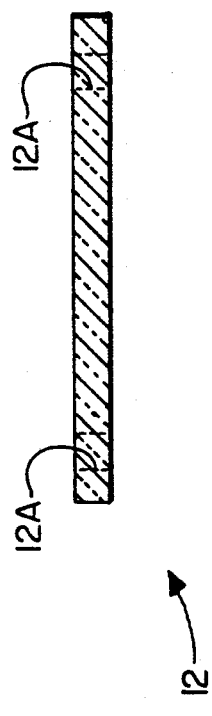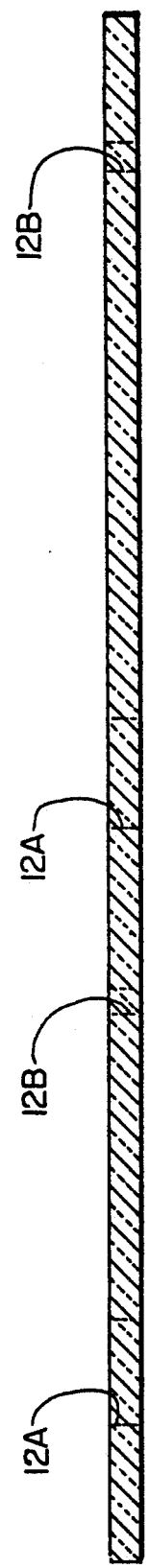

MULTI-PURPOSE EMERGENCY ROOM TRAUMA BOARD

TECHNICAL FIELD

The present invention relates generally to emergency room trauma boards, and more particularly to an improved multi-purpose emergency room trauma board adapted for use both in emergency room procedures as well as in subsequent procedures at other hospital locations.

RELATED ART

As is well known to those who have familiarity with hospital emergency rooms, trauma victims are typically brought to a hospital emergency room on a wooden backboard in an immobilized state. In the emergency room, the victim is transferred from the wooden backboard to an emergency room examining table and/or X-ray table during the examination and initial X-ray process. X-rays are obtained of the chest, abdominal and/or pelvic areas by means of lifting the victim sufficiently to position an X-ray cassette beneath the chest, abdomen and/or pelvic area prior to taking of X-rays and then again lifting the patient subsequent to the X-rays in order to remove the X-ray cassette.

After the examination and initial X-rays of the patient in the hospital emergency room, the victim is transferred from the emergency room examining table or X-ray table onto another apparatus for transfer to the next phase in the resuscitation process such as the operating room, the radiology department, or another section of the emergency room.

Unfortunately, the repeated transfer and/or movement of the trauma victim during the aforementioned initial examination and/or diagnostic procedures can be very harmful and can even result in the death of a gravely injured trauma victim. Also, the continuous movement and transfer of the trauma victim exposes the hospital emergency room personnel to infectious agents (such as HIV) due to the absorption of blood and/or other body fluids from a severely injured patient.

Thus, there is undeniably a long-felt need for a replacement for the conventional wooden trauma board which would minimize the need to move a trauma victim during emergency room procedures and treatment immediately subsequent thereto as well as to minimize the contact of emergency room personnel with blood and other body fluids of the trauma victim. Applicants have invented a new multi-purpose emergency room trauma board which successfully addresses both of these well-known problems associated with conventional wooden trauma backboards.

Of interest, U.S. Pat. No. 4,947,418 to Barr et al. for an "Emergency Trauma Board" represents an effort to overcome some of the problems associated with wooden trauma backboards. The Barr et al. reference discloses a somewhat complicated emergency room trauma board comprising an upper metal frame supporting a rigid translucent plastic panel therein and a lower spaced-apart metal frame supporting a fluid permeable patient support web therein. The spaced-apart upper and lower frames include a plurality of channels therebetween for receiving X-ray cassettes as well as a mechanical gear drive and bracing mechanism for pivotably raising the upper plastic patient support surface to position an immobilized trauma patient on his side to prevent aspiration and the like. X-rays may be taken when a patient is on the top plastic patient support surface or, if the trauma board is inverted, the patient may be positioned on the support web to provide air ventilation to the patient as well as to accommodate the free passage of cleansing fluid therethrough during certain emergency procedures involving irrigation for chemical contamination and the like.

Although the Barr et al. trauma board is well intended in concept, it suffers significant shortcomings in practice and, to applicants' best information and belief, has never been successfully commercialized. For example, the emergency trauma board limits the placement of X-ray cassettes to only specific locations and the complex gear mechanism thereof is not practical for expeditious elevation of a victim. Also, the trauma board provides no means of preventing contact with blood and other body fluids during use and, due to its complex construction, it would be difficult to clean blood and other body fluids from the trauma board subsequent to use thereof. Still further, the trauma board is limited exclusively to use in the hospital emergency room and a trauma victim must be transferred therefrom prior to subsequent examination and/or procedures in the operating room, fluoroscopy department, etc.

Therefore, the search for a more perfect emergency room trauma board which limits the necessity to manipulate and/or transfer a trauma victim as well as the exposure of emergency room personnel to the blood and other body fluids of the trauma victim has continued until the development of applicants' inventive trauma board which will be described in specific detail hereinbelow.

DISCLOSURE OF THE INVENTION

In accordance with the present invention, applicants provide a multi-purpose emergency room trauma board designed specifically to minimize the necessity for manipulation and transfer of a trauma victim as well as to minimize the exposure of emergency room personnel to the blood and other body fluids of the trauma victim. The trauma board of the invention comprises a rigid, non-porous plastic backboard defining a patient support surface on one side thereof. A rigid, fluid impermeable base defining a top surface area at least equal to the patient support surface of the backboard is also provided which comprises an elevated lip around the perimeter thereof to maintain body fluids within the top surface area of the base. Support means are mounted on the rigid base and adapted to removably support the backboard thereon in a substantially parallel and spaced-apart relationship and at a sufficient height to allow for slidably positioning an X-ray cassette between the backboard and the base. In this fashion, a trauma patient on the trauma board may have selected X-rays taken of their upper and/or lower body in a hospital emergency room and then be transported on the removable backboard portion of the trauma board for subsequent post-emergency room treatment and/or procedures.

It is therefore the object of the present invention to provide a multi-purpose emergency room trauma board which facilitates emergency room procedures on the patient and subsequent transferring of the patient from the emergency room for post-emergency room procedures without requiring manipulation or transference of the patient from the trauma board.

It is another object of the present invention to provide a multi-purpose trauma board which is adapted to contain the blood and/or other body fluids from the trauma patient within a specifically defined area in the base thereof so as to minimize contact of emergency room personnel therewith and to thereby minimize the health risk to the emergency personnel.

It is still another object of the present invention to provide a multi-purpose emergency room trauma board which is adapted to facilitate the taking of upper and/or lower body X-rays of the trauma victim without necessitating manipulation of the trauma victim and to then allow for the trauma victim to be transported on the removable upper plastic backboard thereof directly to another location for subsequent examination and/or procedures while still being maintained on the plastic backboard.

It is yet another object of the present invention to provide a multi-purpose emergency room trauma board which is simple in construction and which may be easily cleaned subsequent to use thereof in the hospital emergency room.

Some of the objects of the invention having been stated, other objects will become evident as the description proceeds, when taken in connection with the accompanying drawings described immediately hereinbelow.

BRIEF DESCRIPTION OF THE DRAWINGS

FIG. 4 is a lateral cross-sectional view taken substantially along line 4—4 of FIG. 2;

FIG. 5 is a lengthwise cross-sectional view taken substantially along line 5—5 of FIG. 2;

BEST MODE FOR CARRYING OUT THE INVENTION

Figure 1:
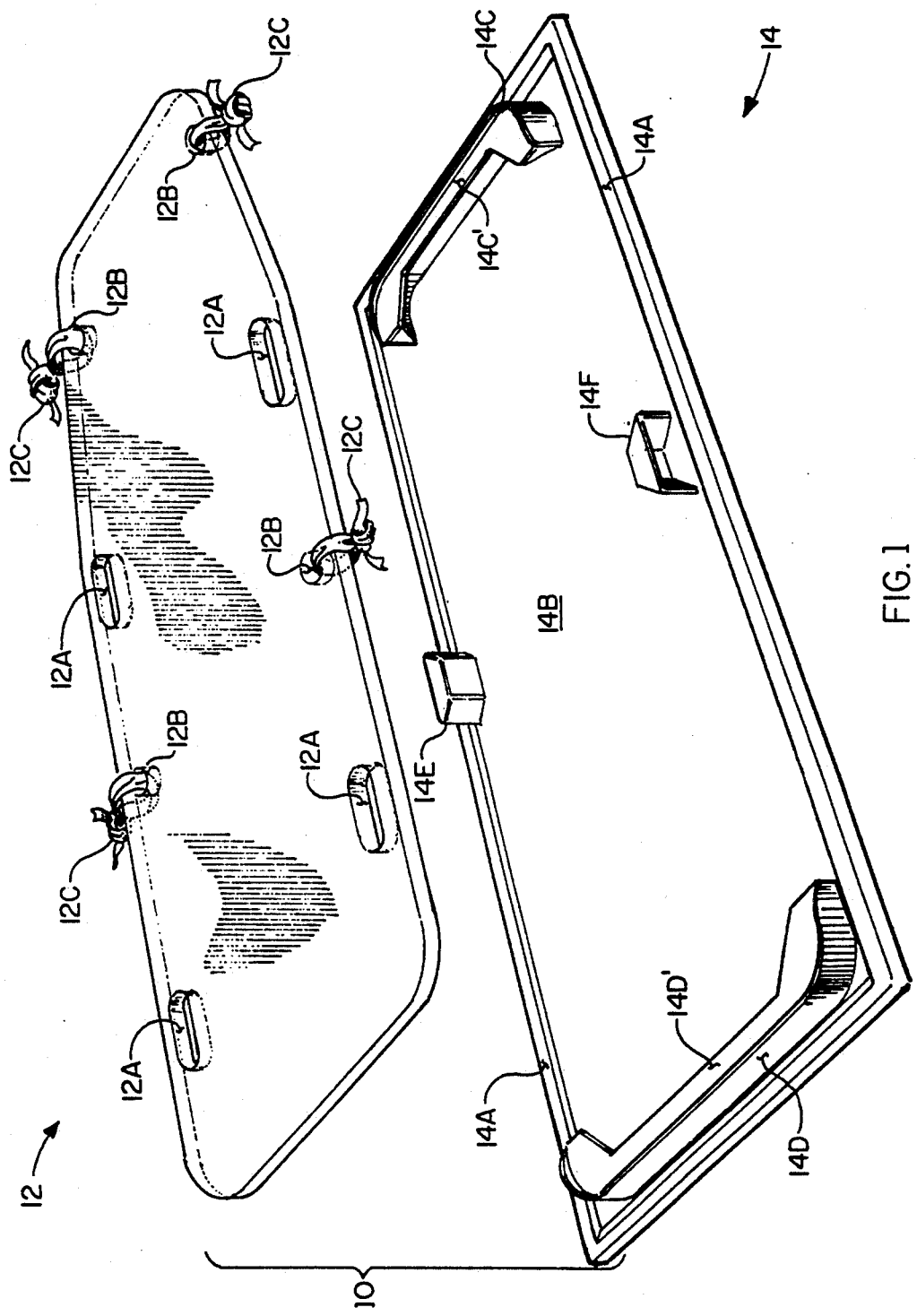
FIG. 1 is an exploded perspective view of a multi-purpose emergency room trauma board embodying the invention.
Figure 2:
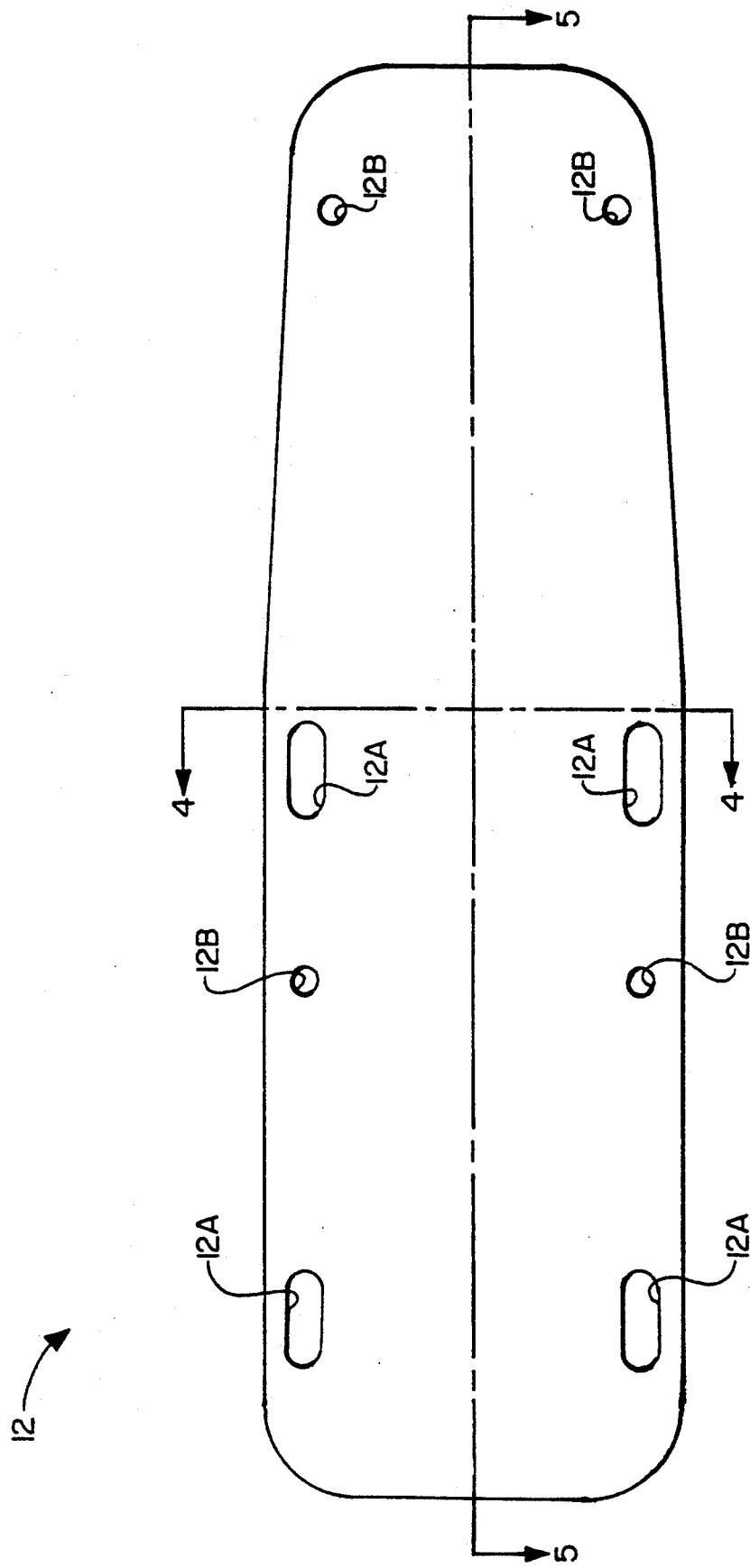
FIG. 2 is a top plan view of the plastic backboard of the multi-purpose emergency room trauma board shown in FIG. 1.
Figure 3:
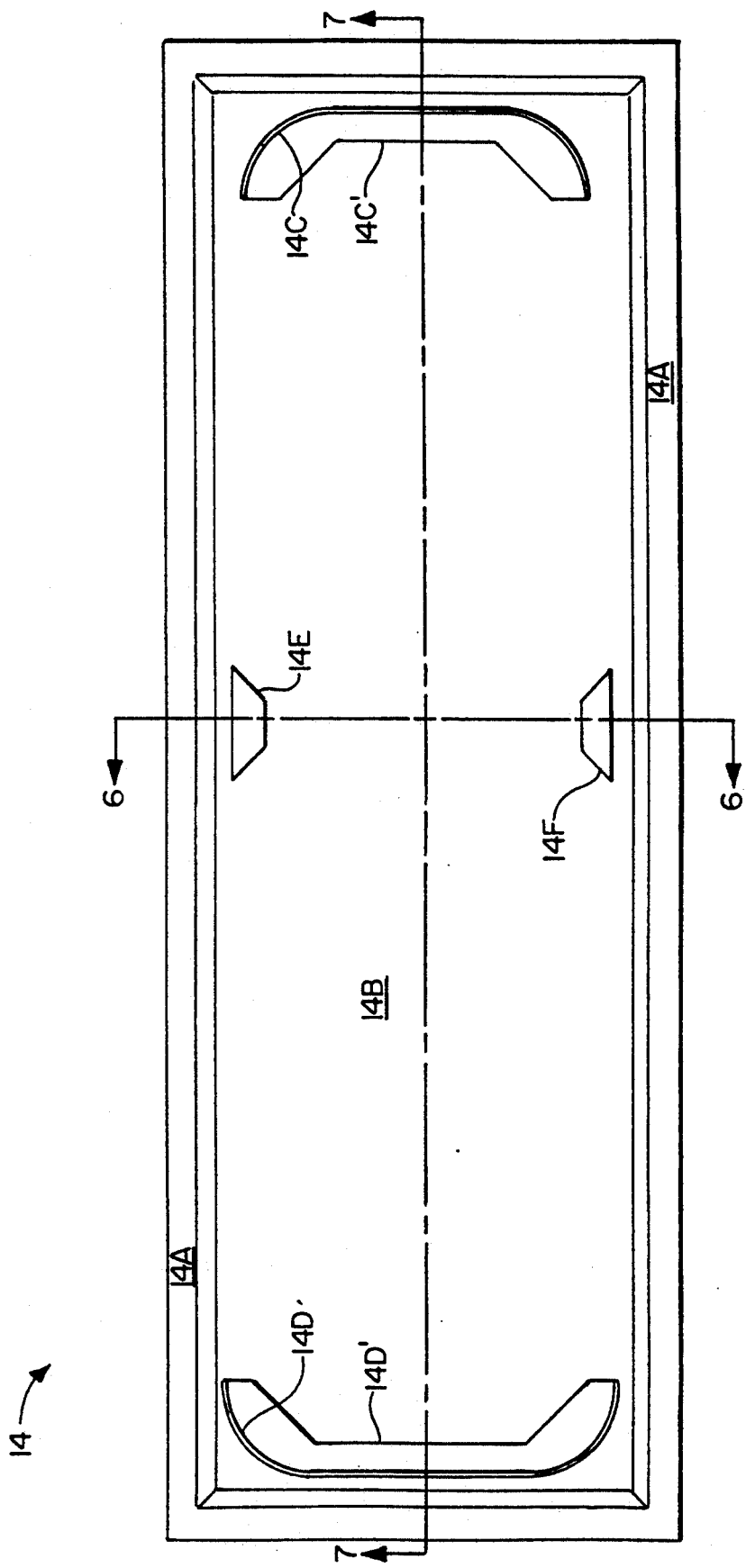
FIG. 3 is a top plan view of the fluid impermeable base of the multi-purpose emergency room trauma board shown in FIG. 1.
Figure 6:
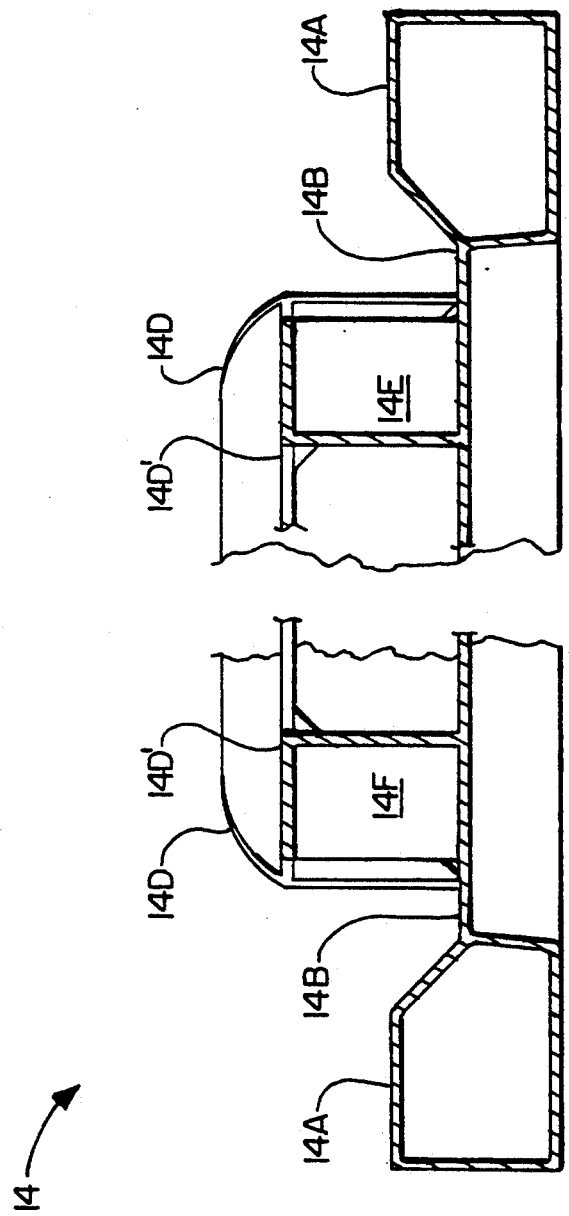
FIG. 6 is a lateral cross-sectional view taken substantially along line 6—6 of FIG. 3.
Figure 7:
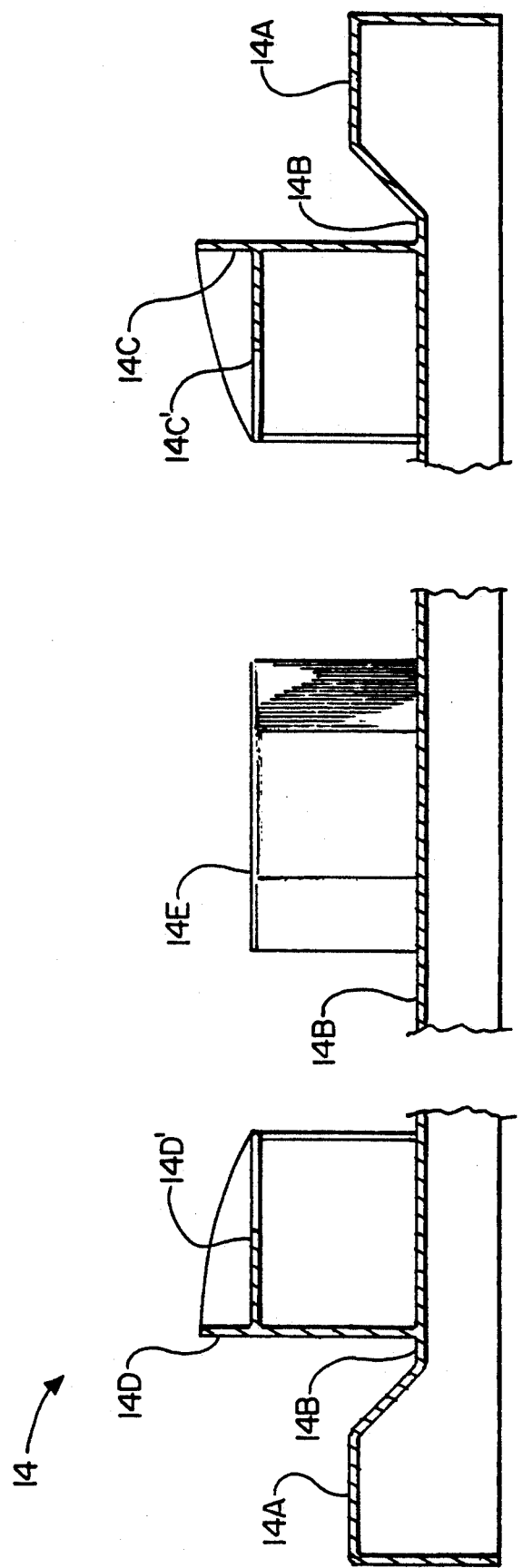
FIG. 7 is a lengthwise cross-sectional view taken substantially along line 7—7 of FIG. 3.

The multi-purpose emergency room trauma board of the present invention would most suitably be kept on a stretcher in the trauma room of a hospital emergency department or room. When a trauma patient is brought into the emergency department or room, the patient most probably would be brought in on a conventional wooden backboard by emergency medical personnel who will then place the trauma victim onto the multi-purpose trauma board of the invention. Typically, the trauma patient is log rolled off the wooden backboard onto the inventive trauma board in a conventional and well-known technique.

Once positioned on the multi-purpose trauma board of the invention, an X-ray technician will typically position an X-ray cassette into a position defined in the space between the backboard and the spaced-apart base of the multi-purpose trauma board to obtain desired chest, abdominal and/or pelvic films which are necessary in all trauma cases. Once the emergency room X-rays are taken and the X-ray cassettes removed from the multi-purpose trauma board, the backboard portion of the multi-purpose trauma board is removed from the base with the trauma patient thereon and then transported to the next phase in the resuscitation process which typically is the radiology department, operating room or another section of the emergency department or room. Thereafter, the base of the multi-purpose trauma board is cleaned and another unused backboard positioned thereon for use with the next trauma patient.

Referring now to the drawings for a complete understanding of the present invention, a multi-purpose emergency room trauma board embodying the invention is generally designated 10 and comprises backboard 12 and base 14. Backboard 12 is preferably formed from a rigid translucent lightweight plastic which is easily penetrable by X-ray and CT scanning equipment and which will not absorb blood and other body fluids. Backboard 12 is most suitably formed from LEXAN or PLEXIGLAS and can be easily cleaned with conventional cleaning agents. Also, backboard 12 is provided with apertures 12A and 12B therein. Apertures 12A serve as handles by which backboard 12 may be carried, and apertures 12B provide a location for receiving flexible restraint straps therein in order to restrain a trauma victim, as may be desired, while positioned on backboard 12 of multi-purpose trauma board 10.

The translucent plastic from which backboard 12 is formed allows for ease of placement of X-ray cassettes in the space defined between backboard 12 and base 14 by X-ray technicians in order to facilitate emergency room X-ray procedures without manipulation of the body of the trauma victim. Also, and as would be apparent to one familiar with X-ray equipment, plastic backboard 12 allows for X-rays to pass easily therethrough to obtain clear and unobstructed images of the body portion of interest of the trauma victim.

Although substantially any type of flexible restraint straps could be used in either apertures 12A or 12B, applicants presently contemplated that the use of disposable restraint straps 12C is particularly desirable. In addition to patient restraint, restraint straps 12C may be used by medical personnel to lift and carry backboard 12.

Although not absolutely necessary, applicants' contemplate that a preferred use of the instance invention would include providing a non-porous, urethane coated table pad on backboard 12 to enhance the comfort of the trauma patient thereon and to prevent bedsores and the like. The table pad (not shown in drawings) is available from A.A.D.C.O. Inc. of Boston, Mass.

Base 14 is preferably formed from a rigid lightweight stainless steel (preferably 16-gauge) that can be easily positioned onto conventional stretchers. Very significantly, base 14 includes a raised lip 14A around the circumference thereof which defines a recessed well 14B in the top surface of stainless steel base 14 to catch and retain overflow blood and other body fluids from the trauma victim so as to decrease the exposure of health care personnel thereto. This is particularly advantageous since the exposure of health care personnel to the blood and body fluids of trauma victims is of increasing concern in view of the HIV, hepatitis and other diseases which could potentially be carried in the blood and/or other body fluids of the trauma victim. In this regard, the trauma setting is especially worrisome and the containment feature of applicants' invention especially desirable since trauma patients are normally not sedated and health care personnel tending to the patient may be exposed to massive amounts of blood and body fluids.

Rigid but lightweight stainless steel base 14 is also provided with upstanding support struts 14C, 14D at the lower and upper ends thereof, respectively. Upstanding support struts 14C and 14D are most suitably also formed of stainless steel and configured so as to abuttingly receive backboard 12 on ledges 14C' and 14D', respectively, in vertically spaced apart and parallel relationship to base 14. The vertical space defined between backboard 12 and base 14 allows X-ray cassettes to be easily positioned at any selected site from head to toe of the trauma patient, and health care personnel can continue to work on the trauma patient while X-ray technicians insert and remove cassettes during emergency room X-ray procedures. In order to fully support backboard 12 on base 14, additional upstanding support struts 14E and 14F (also formed of stainless steel) are provided on opposing sides of base 14 to provide medial support to backboard 12.

Advantageously, multi-purpose trauma board 10 is most suitably of a standardized size to fit into ambulances as well known CT scanners. This allows for trauma victims to be placed upon multi-purpose trauma board 10 as early as during initial resuscitation in the field and to remain thereon in the hospital emergency department or room and to continue on backboard 12 thereof during transport from the emergency room to the hospital X-ray department, operating room, or other necessary treatment area. Representative dimensions for the preferred embodiment of multi-purpose trauma board 10 are as follows:

| Backboard | |
|---|---|
| Length: | 71.25 inches |
| Width at head end: | 22 inches |
| Width at foot end: | 19.50 inches |
| Construction material: | .50 inch thick LEXAN |
| Base | |
| Length: | 74 inches |
| Width at head end: | 26 inches |
| Width at foot end: | 26 inches |
| Height: | 1.50 inches |
| Depth of recessed portion (or drip pan): | .1875 inches |
| Height defined between drip pan and backboard: | 1.5 inches |
| Height of end support struts | 2.25 inches |
| Height of side support struts | 1.5 inches |
| Construction material: | 16 gauge stainless steel |

Thus, applicants' novel multi-purpose trauma board provides the dual advantages of (1) minimizing the need to manipulate and transfer trauma victims during the X-ray procedure in the emergency room and during transfer therefrom for subsequent diagnosis and/or procedures and (2) minimizing the risk of exposure of emergency health care personnel to infectious agents contained within the blood and body fluids of the trauma victim. The elegantly simple and yet ingenious apparatus of the invention simultaneously accomplishes both objectives to provide a highly desirable multi-purpose emergency room trauma board which has been extremely well received during initial testing in selected hospital emergency rooms.

It will be understood that various details of the invention may be changed without departing from the scope of the invention. Furthermore, the foregoing description is for the purpose of illustration only, and not for the purpose of limitation—the invention being defined by the claims.

What is claimed is:

1. A multi-purpose emergency room trauma board for handling trauma victims during emergency treatment, comprising:
    a rigid, non-porous plastic backboard defining a patient support surface on one side thereof;
    a rigid, fluid impermeable base defining a top surface area at least equal to the patient support surface area of said backboard and comprising an elevated lip around the perimeter thereof to maintain patient body fluids within the top surface area of said base circumscribed by said lip; and
    support means mounted on said rigid base and adapted to removably support said backboard thereon in a substantially parallel and spaced-apart relationship to said base sufficient in height to allow for slidably positioning an X-ray cassette between said backboard and said base;
    whereby a patient on said trauma board may have selective X-rays taken of their upper and/or lower body in a hospital emergency room and then be transported on said backboard portion of said trauma board for subsequent post emergency room treatment and/or procedures.

2. A multi-purpose emergency room trauma board according to claim 1 wherein said backboard is formed of X-ray penetrable plastic.

3. A multi-purpose emergency room trauma board according to claim 2 wherein said plastic is translucent.

4. A multi-purpose emergency room trauma board according to claim 2 wherein said backboard defines a first plurality of apertures therein for removably receiving flexible restraint straps therein and a second plurality of apertures therein adapted to serve as handles to facilitate removal of said backboard from said base and carrying of said backboard.

5. A multi-purpose emergency room trauma board according to claim 1 wherein said base is formed from stainless steel.

6. A multi-purpose emergency room trauma board according to claim 5 wherein said base is substantially rectangular in shape.

7. A multi-purpose emergency room trauma board according to claim 1 wherein said support means comprises an upstanding support element at each of two opposing ends of said base adapted to abuttingly receive said backboard thereon.

8. A multi-purpose emergency room trauma board according to claim 7 wherein said support means further comprises a plurality of upstanding supports mounted between said upstanding support elements for supporting the medial portion of said backboard thereon.

9. A multi-purpose emergency room trauma board for handling trauma victims during emergency treatment, comprising:
    a rigid, non-porous plastic unitary backboard defining a patient support surface on one side thereof, said backboard being formed from an X-ray penetrable plastic;
    a rigid, fluid impermeable unitary base defining a top surface area at least equal to the patient support surface area of said backboard and comprising an elevated lip around the perimeter thereof to maintain patient body fluids within the top surface area of said base circumscribed by said lip, said base being formed from stainless steel; and support means mounted on said rigid base and adapted to removably support said backboard thereon in a substantially parallel and spaced-apart relationship to said base sufficient in height to allow for slidably positioning an X-ray cassette between said backboard and said base;

whereby a patient on said trauma board may have selective X-rays taken of their upper and/or lower body in a hospital emergency room and then be transported on said backboard portion of said trauma board for subsequent post emergency room treatment and/or procedures.

10. A multi-purpose emergency room trauma board according to claim 9 wherein said backboard is translucent.

11. A multi-purpose emergency room trauma board according to claim 9 wherein said backboard defines a first plurality of apertures therein for removably receiving flexible restraint straps therein and a second plurality of apertures therein adapted to serve as handles to facilitate removal of said backboard from said base and carrying of said backboard.

12. A multi-purpose emergency room trauma board according to claim 9 wherein said base is substantially rectangular in shape.

13. A multi-purpose emergency room trauma board according to claim 9 wherein said support means comprises an upstanding support element at each of two opposing ends of said base and adapted to abuttingly receive said backboard thereon.

14. A multi-purpose emergency room trauma board according to claim 13 wherein said support means further comprises a plurality of upstanding supports mounted between said upstanding support elements for supporting the medial portion of said backboard thereon.

* * * * *